(12) United States Patent
Cheng et al.

(10) Patent No.: US 10,529,071 B2
(45) Date of Patent: *Jan. 7, 2020

(54) FACIAL SKIN MASK GENERATION FOR HEART RATE DETECTION

(71) Applicant: Microsoft Technology Licensing, LLC, Redmond, WA (US)

(72) Inventors: Beibei Cheng, Redmond, WA (US); Benjamin William Walker, Redmond, WA (US); Jonathan Ross Hoof, Redmond, WA (US); Daniel Kennett, Redmond, WA (US); Anis Ahmad, Redmond, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/036,792

(22) Filed: Jul. 16, 2018

(65) Prior Publication Data

US 2019/0073767 A1 Mar. 7, 2019

Related U.S. Application Data

(63) Continuation of application No. 15/406,181, filed on Jan. 13, 2017, now Pat. No. 10,026,171, which is a (Continued)

(51) Int. Cl.
*G06T 7/00* (2017.01)
*G06T 7/90* (2017.01)
(Continued)

(52) U.S. Cl.
CPC ............ *G06T 7/0012* (2013.01); *A61B 5/024* (2013.01); *G06K 9/00234* (2013.01);
(Continued)

(58) Field of Classification Search
CPC ......... G06T 7/0014; G06T 2207/10048; G06T 2207/30088; G06T 7/90;
(Continued)

(56) References Cited

U.S. PATENT DOCUMENTS

2013/0096439 A1* 4/2013 Lee .................. A61B 5/024
600/479
2014/0072190 A1* 3/2014 Wu ................... G06T 7/262
382/128
(Continued)

FOREIGN PATENT DOCUMENTS

CN 101371566 A 2/2009
CN 102448564 A 5/2012

OTHER PUBLICATIONS

"Office Action Issued in European Patent Application No. 15788526. 0", dated Mar. 26, 2019, 06 Pages.
(Continued)

*Primary Examiner* — Yon J Couso
(74) *Attorney, Agent, or Firm* — Davin Chin; Chin IP, PLLC

(57) ABSTRACT

A facial skin mask may be generated based on isolating a head part in a captured image, removing a first pixel that is indicative of non-skin from the head part in the captured image, and removing a second pixel that is indicative of having a high velocity from the head part in the captured image. Heart rate may be detected based on the change of color of the pixels of the generated facial skin mask.

20 Claims, 7 Drawing Sheets

Related U.S. Application Data continuation of application No. 14/518,596, filed on Oct. 20, 2014, now Pat. No. 9,582,879.

(51) Int. Cl.
| | | |
|---|---|---|
| *A61B 5/024* | (2006.01) | |
| *G06K 9/00* | (2006.01) | |
| *G06T 7/50* | (2017.01) | |
| *G06T 7/70* | (2017.01) | |
| *G06K 9/62* | (2006.01) | |
| *G06T 11/60* | (2006.01) | |
| *H04N 5/33* | (2006.01) | |

(52) U.S. Cl.
CPC ....... *G06K 9/00335* (2013.01); *G06K 9/6267* (2013.01); *G06T 7/0014* (2013.01); *G06T 7/50* (2017.01); *G06T 7/70* (2017.01); *G06T 7/90* (2017.01); *G06T 11/60* (2013.01); *H04N 5/33* (2013.01); *G06T 2207/10024* (2013.01); *G06T 2207/10048* (2013.01); *G06T 2207/30048* (2013.01); *G06T 2207/30088* (2013.01); *G06T 2207/30196* (2013.01)

(58) Field of Classification Search
CPC ........... G06T 2207/30048; G06T 11/60; G06T 7/0012; G06T 7/70; G06T 7/50; G06T 2207/30196; G06T 2207/10024; G06K 9/00335; G06K 9/00234; G06K 9/6267; A61B 5/024; H04N 5/33
See application file for complete search history.

(56) References Cited

U.S. PATENT DOCUMENTS

| | | | | |
|---|---|---|---|---|
| 2014/0088433 | A1* | 3/2014 | Shan | A61B 5/1128 600/473 |
| 2014/0161421 | A1* | 6/2014 | Shoemaker | G11B 27/028 386/278 |
| 2016/0253820 | A1* | 9/2016 | Jeanne | A61B 5/7207 382/107 |
| 2016/0317041 | A1* | 11/2016 | Porges | A61B 5/7235 |
| 2016/0345832 | A1* | 12/2016 | Pavagada Nagaraja | A61B 5/0022 |

OTHER PUBLICATIONS

"First Office Action and Search Report Issued in Chinese Patent Application No. 201580057096.8", dated Sep. 25, 2019, 17 Pages.

* cited by examiner

FACIAL SKIN MASK GENERATION FOR HEART RATE DETECTION

CROSS-REFERENCE TO RELATED APPLICATION(S)

This application is a continuation of U.S. patent application Ser. No. 15/406,181, filed Jan. 13, 2017, entitled "FACIAL SKIN MASK GENERATION FOR HEART RATE DETECTION", which is a continuation of U.S. patent application Ser. No. 14/518,596, filed Oct. 20, 2014, entitled "FACIAL SKIN MASK GENERATION FOR HEART RATE DETECTION," now U.S. Pat. No. 9,582,879, issued Feb. 28, 2017. The entirety of each of these afore-mentioned application(s) is incorporated herein by reference.

BACKGROUND

Optical heart rate monitoring systems typically use an optical radiation sensor that is sensitive to visible or infrared (IR) light to detect the flow of hemoglobin in blood in the human body. In some systems, a subject wears some form of monitoring equipment or a sensor is positioned to contact an extremity such as a finger or earlobe. Contact systems can often be cumbersome and impractical for application to athletes, fitness enthusiasts, or ambulatory medical patients.

This Background is provided to introduce a brief context for the Summary and Detailed Description that follow. This Background is not intended to be an aid in determining the scope of the claimed subject matter nor be viewed as limiting the claimed subject matter to implementations that solve any or all of the disadvantages or problems presented above.

SUMMARY

Data is received of a captured image; the data of the captured image includes a subset of data of an anatomical head. The subset of data of the anatomical head includes a plurality of representative pixels having a respective plurality of pixel values. It may be determined that each pixel of the plurality of representative pixels has the respective plurality of pixel values within a threshold value that is indicative of skin.

It should be appreciated that the above-described subject matter may be implemented as a computer-controlled apparatus, a computer process, a computing system, or as an article of manufacture such as one or more computer-readable storage media. These and various other features will be apparent from a reading of the following Detailed Description and a review of the associated drawings.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. Furthermore, the claimed subject matter is not limited to implementations that solve any or all disadvantages noted in any part of this disclosure.

BRIEF DESCRIPTION OF THE DRAWINGS

Like reference numerals indicate like elements in the drawings. Elements are not drawn to scale unless otherwise indicated.

DETAILED DESCRIPTION OF ILLUSTRATIVE EXAMPLES

Disclosed herein is the use of a facial skin mask that may be used for various applications, such as heart rate detection or displaying visual effects. The facial skin mask may be generated based on isolating a head part in a captured image, removing pixels that are indicative of not skin from the head part in the captured image, and removing pixels that are indicative of having a high velocity from the head part in the captured image. The pixel values of the head part of a converted captured image can act as a confidence level of whether a pixel is skin or not skin. After skin or not skin is determined, a subject's heart rate can be determined by tracking the change of the subject's skin color from one frame to the next frame that is caused by oxygenated blood flooding during a heartbeat.

Figure 1:
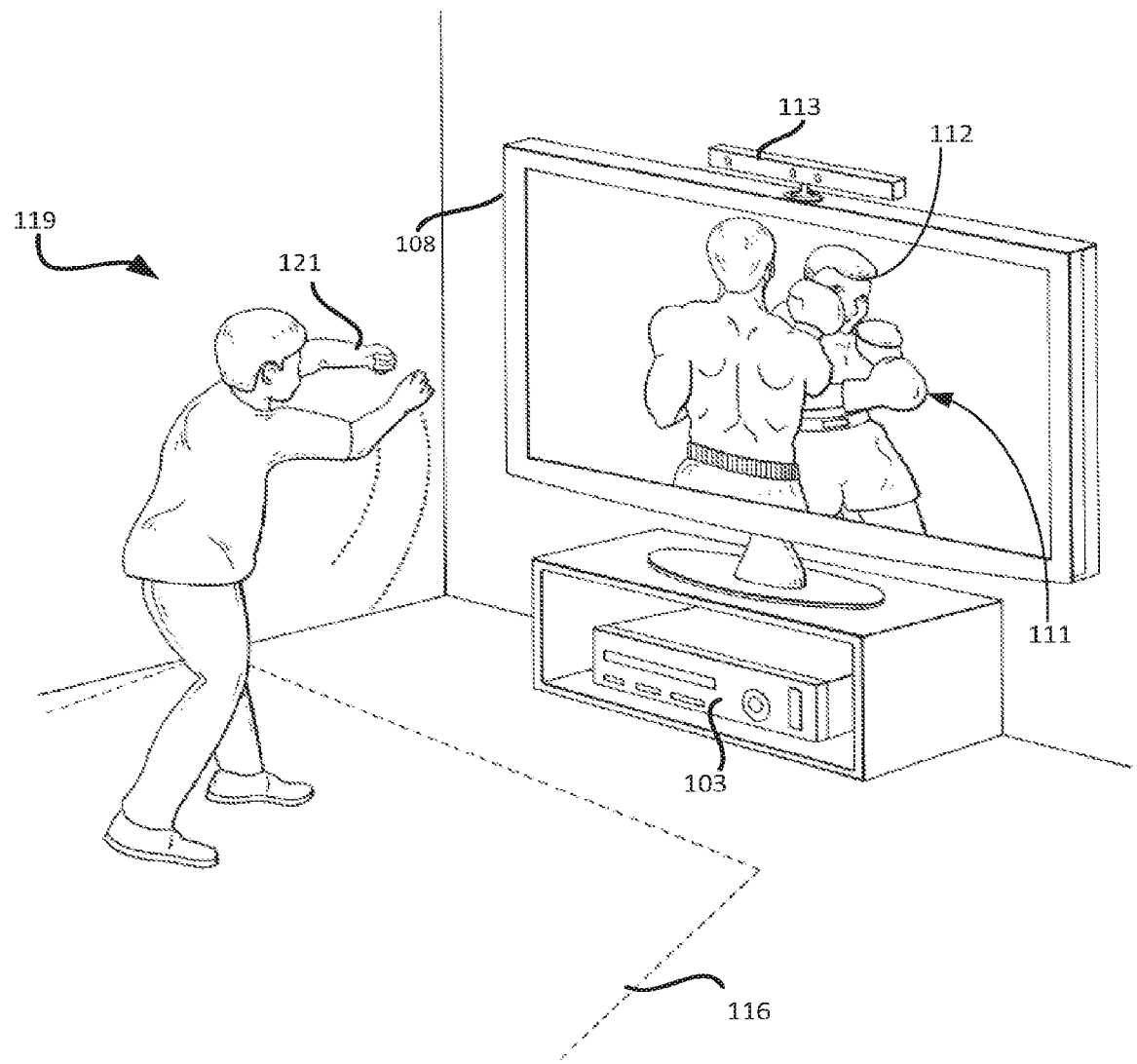
FIG. 1 illustrates an exemplary environment for the disclosed facial skin mask.

FIG. 1 illustrates an exemplary environment 100 in which the disclosed optical heart rate tracking may be implemented. It is emphasized that the environment 100 is intended to be illustrative and that other environments which include other types of devices, applications, and usage scenarios may also be able to utilize the principles described herein. The environment 100 includes a computing platform such as multimedia console 103 that is typically configured for running gaming and non-gaming applications using local and/or networked programming and content, playing pre-recorded multimedia such as optical discs including digital versatile discs (DVDs) and Blu-ray discs, streaming multimedia from a network, participating in social media, browsing the Internet and other networked media and content, or the like using a coupled audio/visual display 108, such as a television.

The multimedia console 103 in this example is operatively coupled to a capture device 113 which may be implemented using one or more video cameras that are configured to visually monitor a physical space 116 (indicated generally by the dashed line in FIG. 1) that is occupied by a user 119. As described below in more detail, the capture device 113 is configured to capture, track, and analyze the movements of the user 119. The movements may be used as controls that may be employed to affect, for example, an application or an operating system running on the multimedia console 103. Various motions of the hand 121 or other body parts of the user 119 may correspond to common system wide tasks such as selecting a game or other application from a main user interface.

Display 108 provides a visual representation of a boxing opponent to the user 119 as well as a visual representation of a player avatar 111 that has a captured image head part 112. The captured image head part 112 may be a captured image of the user 119 with overlaid visual effects as discussed in more detail herein. The user 119 may make movements (e.g., throwing a punch) in the physical space 116 to cause the player avatar to make a corresponding movement in the game space. Movements of the user 119 may be recognized and analyzed in the physical space 116 such that corresponding movements for game control of the player avatar in the game space are performed.

Gaming applications supported by the multimedia console 103 provide an exemplary context in which the disclosed facial mask generation and optical heart rate tracking may be advantageously utilized. For example with regard to optical heart rate tracking, in the boxing game discussed above, a game designer may wish to add a game feature in which a user's heart rate is monitored along with other factors (such as number of punches thrown and landed per round) as an indication of the user's performance, skill, or fitness level. With regard to the disclosed facial mask generation in particular, areas of the face (e.g., eyes, teeth, and mouth) and composition of the face (e.g., hair and facial skin) may be more accurately identified and therefore visual effects may be accurately applied. The disclosed facial skin mask generation may be used to create anchor points that can help track the face of the user 119 in a meaningful way. For example, during the boxing match a captured image of the user 119 may be shown on the display 108. The captured image head part 112 may be a captured image of the head of user 119 that may be overlaid with realistic scars and bruises on a cheek of the user 119, which may pulse in sequence with the heart rate of user 119. Other augmented reality effects may also be applied, such as a visual depiction of blood vessels of the user 119 flashing in sequence with a measured heart rate. It will be further appreciated that heart rate tracking may be useful in other contexts including both gaming and non-gaming contexts.

Figure 2:
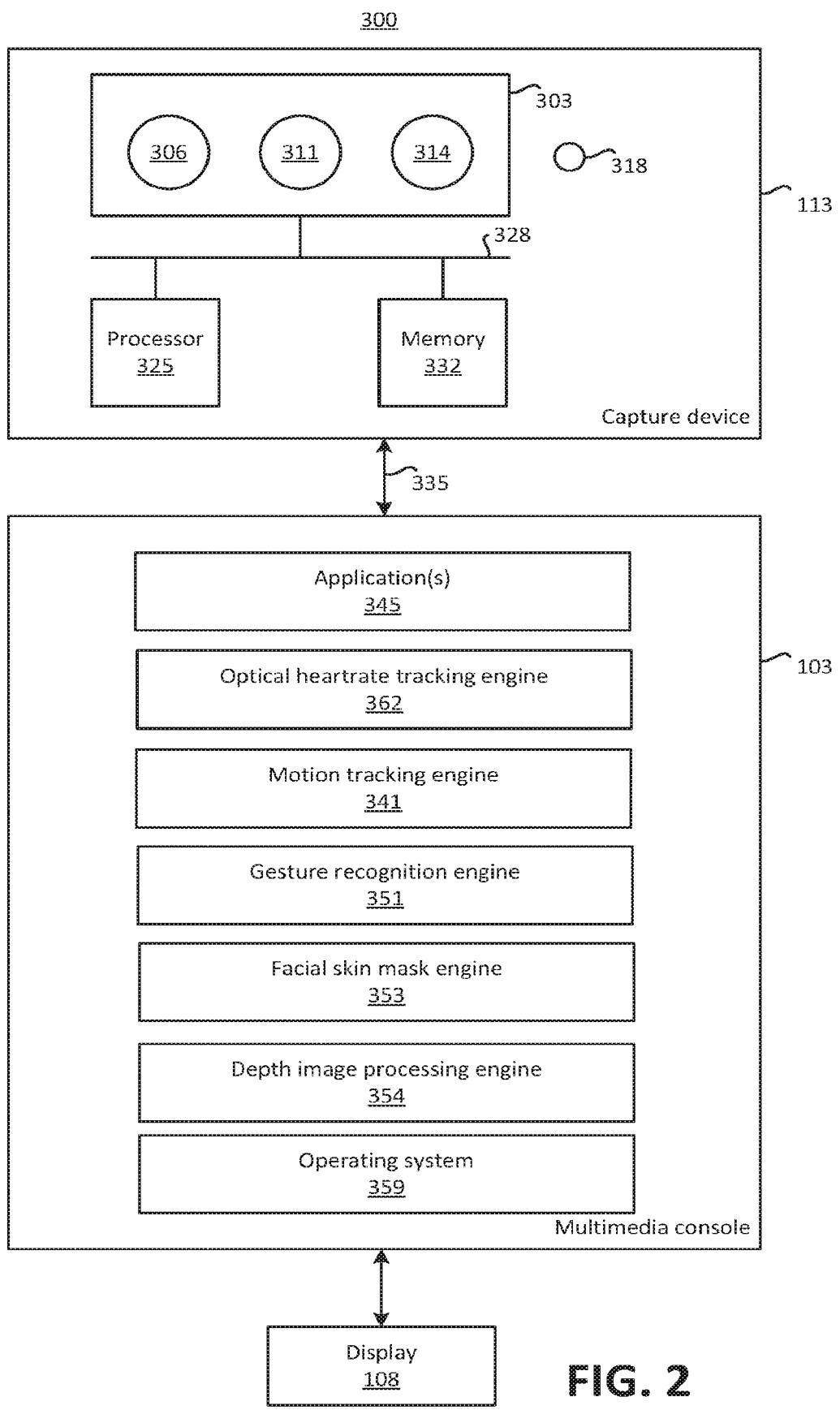
FIG. 2 illustrates an exemplary capture device that may be used in part to create the disclosed facial skin mask.

FIG. 2 illustrates exemplary functional components of the capture device 113 that may be used as part of a target recognition, analysis, and tracking system 300 to recognize human and non-human targets in a capture area of the physical space 116 (FIG. 1) without the use of special sensing devices attached to the subjects, uniquely identify them, and track them in three-dimensional space. The capture device 113 may be configured to capture video with depth information including a depth image that may include depth values via any suitable technique including, for example, time-of-flight, structured light, stereo image, or the like. In some implementations, the capture device 113 may organize the calculated depth information into "Z layers," or layers that may be perpendicular to a Z-axis extending from the depth camera along its line of sight.

As shown in FIG. 2, the capture device 113 includes an image camera component 303. The image camera component 303 may be configured to operate as a depth camera that may capture a depth image of a scene. The depth image may include a two-dimensional (2D) pixel area of the captured scene where each pixel in the 2D pixel area may represent a depth value such as a distance in, for example, centimeters, millimeters, or the like of an object in the captured scene from the camera. In this example, the image camera component 303 includes a non-visible light component 306, a non-visible light camera 311 (e.g., IR), and a visible light camera 314 (e.g., YUV or RGB).

Various techniques may be utilized to capture depth video frames. For example, in time-of-flight analysis, the non-visible light component 306 of the capture device 113 may emit an infrared light onto the capture area and may then detect the backscattered light from the surface of one or more targets and objects in the capture area using, for example, the non-visible light camera 311 or the visible light camera 314. In some examples, pulsed infrared light may be used such that the time between an outgoing light pulse and a corresponding incoming light pulse may be measured and used to determine a physical distance from the capture device 113 to a particular location on the targets or objects in the capture area.

The capture device 113 may capture images for visible and non-visible light (radiation) using a single camera or multiple cameras. Non-visible light usually cannot be seen by the ordinary human eye. Examples of non-visible light include infrared (IR), microwave, ultraviolet, X-ray, and gamma-ray. Visible light as associated with humans is usually within the range of 400 nm to 720 nm and an image is typically based on YUV or RGB. The term YUV refers to a family of color spaces, all of which encode brightness information separately from color information. Like RGB, YUV uses three values to represent any color. These values are termed Y', U, and V. YUV is often used as a general term for any color space that works along the same principles as Y'CbCr. The Y' component, also called luma, represents the brightness value of the color. The prime symbol is frequently omitted. The U and V components, also called chroma values or color difference values, are derived by subtracting the Y value from the red and blue components of the original RGB color.

The capture device 113 may further include a microphone 318. The microphone 318 may include a transducer or sensor that may receive and convert sound into an electrical signal. The microphone 318 may be used to reduce feedback between the capture device 113 and the multimedia console 103 in the target recognition, analysis, and tracking system 300. Additionally, the microphone 318 may be used to receive audio signals that may also be provided by the user 119 to control applications such as game applications, non-game applications, or the like that may be executed by the multimedia console 103.

The capture device 113 may further include a processor 325 that may be in operative communication with the image camera component 303 over a bus 328. The processor 325 may include a standardized processor, a specialized processor, a microprocessor, or the like that may execute instructions that may include instructions for storing profiles, receiving the depth image, determining whether a suitable target may be included in the depth image, converting the suitable target into a skeletal representation or model of the target, or any other suitable instruction.

The capture device 113 may further include a memory component 332 that may store the instructions that may be executed by the processor 325, images or frames of images captured by the cameras, user profiles or any other suitable information, images, or the like. According to one example, the memory component 332 may include random access memory (RAM), read only memory (ROM), cache, Flash memory, a hard disk, or any other suitable storage component. As shown in FIG. 2, the memory component 332 may be a separate component in communication with the image capture component 303 and the processor 325. Alternatively, the memory component 332 may be integrated into the processor 325 and/or the image capture component 303. In one example, some or all of the components 303, 306, 311, 314, 318, 325, 328, and 332 of the capture device 113 are located in a single housing. It is contemplated that capture device 113 may be in several different forms based on the implementation. For example the capture device 113 that is communicatively connected with the multimedia console 103 over a communication link 335 may be a video camera, laptop computer with camera, tablet computer with camera, mobile phone with camera, security video camera, video conferencing camera, or the like.

The capture device 113 operatively communicates with the multimedia console 103 over the communication link 335. The communication link 335 may be a wired connection including, for example, a USB (Universal Serial Bus) connection, a Firewire connection, an Ethernet cable connection, or the like. The communication link 335 may be a wireless connection, such as a wireless 802.11 connection. The multimedia console 103 can provide a clock to the capture device 113 that may be used to determine when to capture, for example, a scene via the communication link 335. The capture device 113 may provide the depth information and images captured by, for example, the non-visible light camera 311 or the visible light camera 314, including a skeletal model and/or facial tracking model that may be generated by the capture device 113, to the multimedia console 103 via the communication link 335. The multimedia console 103 may then use the skeletal and/or facial tracking models, depth information, and captured images to create a virtual screen, adapt the user interface, and control an application, for example.

A motion tracking engine 341 uses the skeletal and/or facial tracking models and the depth information to provide a control output to one more applications (representatively indicated by an application 345 in FIG. 3) running on the multimedia console 103 to which the capture device 113 is coupled. The information may also be used by a gesture recognition engine 351, facial skin mask engine 353, depth image processing engine 354, operating system 359, or optical heart rate tracking engine 362. The depth image processing engine 354 uses the depth images to track motion of objects, such as the user and other objects. The depth image processing engine 354 will typically report to operating system 359 an identification of each object detected and the location of the object for each frame. The facial skin mask engine 353 defines a facial skin mask as discussed herein and can typically report to the applications 345, optical heart rate tracking engine 362, or operating system 359. The operating system 359 can use that information to update the position or movement of an avatar, for example, or other images shown on the display 108, or to perform an action on the user interface.

The gesture recognition engine 351 may utilize a gestures library (not shown) that can include a collection of gesture filters, each comprising information concerning a gesture that may be performed, for example, by a skeletal model (as the user moves). The gesture recognition engine 351 may compare the frames captured by the capture device 113 in the form of the skeletal model and movements associated with it to the gesture filters in the gesture library to identify when a user (as represented by the skeletal model) has performed one or more gestures. Those gestures may be associated with various controls of an application. Thus, the multimedia console 103 may employ the gestures library to interpret movements of the skeletal model and to control an operating system or an application running on the multimedia console based on the movements.

Below are exemplary methods associated with facial skin masks. Unless specifically stated, the method as shown below (e.g., FIG. 5-FIG. 7) and those in other methods presented in the drawings and described are not constrained to a particular order or sequence. In addition, some of the methods or steps thereof can occur or be performed concurrently and not all the methods or steps have to be performed in a given implementation depending on the requirements of such implementation and some methods or steps may be optionally utilized. For example, additional processing may be desired in some scenarios to improve the accuracy of identification of skin in certain operating environments at the expense of increased computational and system resource usage. Likewise, some steps may be eliminated in some applications to reduce overhead while decreasing motion tolerance or robustness of a facial skin mask, for example.

Figure 3:
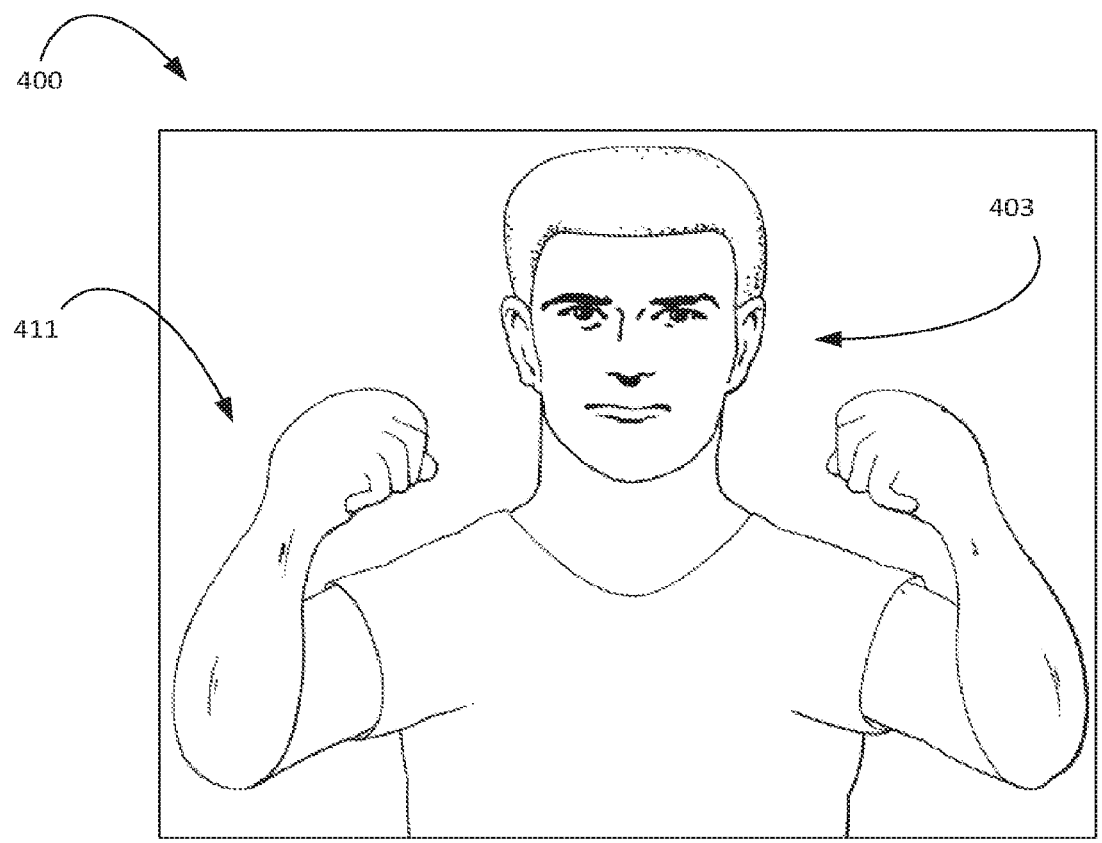
FIG. 3 illustrates an example captured image that may be used for creating a facial skin mask.
Figure 4:
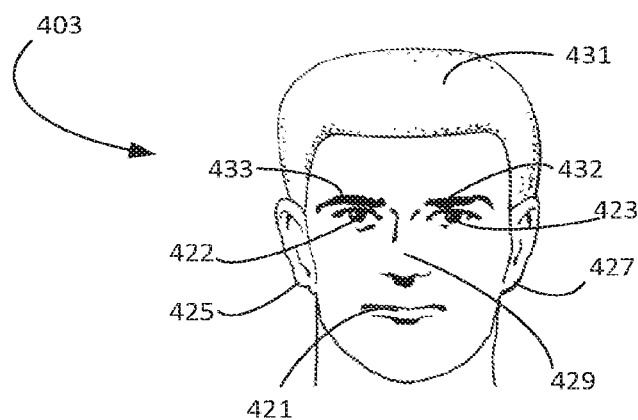
FIG. 4 illustrates a head part of an example captured image that may be used for creating a facial skin mask.

FIG. 3 illustrates an exemplary captured image 400 of an environment. The captured image 400 includes a capture of the user 119 that has a head part 403 and body region 411. FIG. 4 illustrates a close up view of head part 403. Head part 403 has eye 422, eye 423, ear 425, ear 427, mouth 421, nose 429, eye brow 432, eye brow 433, and head hair 431.

Figure 5:
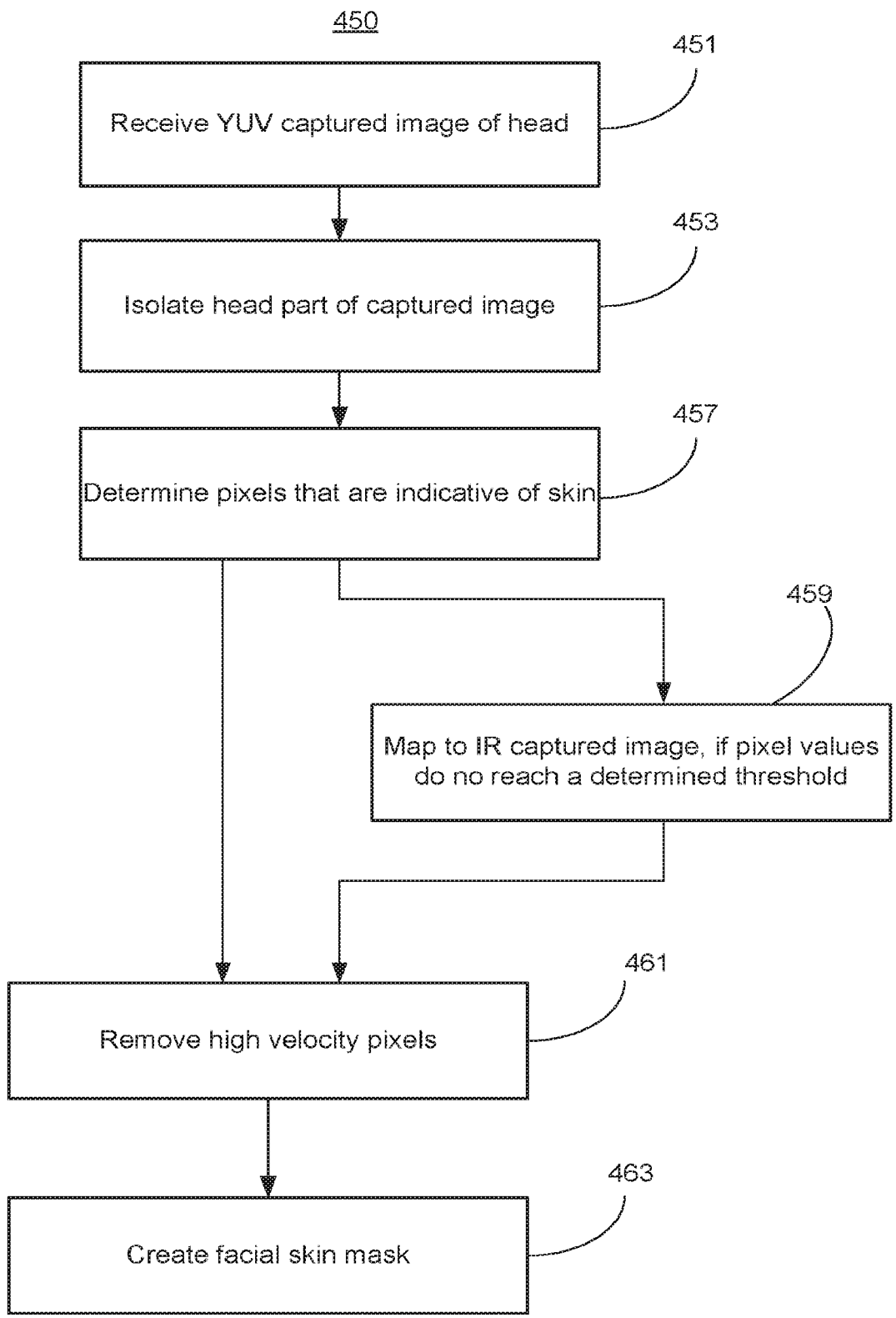
FIG. 5 illustrates an exemplary method for obtaining a facial skin mask.

FIG. 5 is an exemplary method 450 for obtaining a facial skin mask. The method of FIG. 5 as described herein may be executed on console 103 and portions thereof may be executed within facial skin mask engine 353. At block 451 the captured image 400 may be received. Here it is assumed the captured image 400 is a YUV based image captured by the capture device 113. The captured image 400 can be considered data that can be representative of a plurality of pixels for captured image 400. At block 453, a head part 403 (e.g., an anatomical head) is isolated from the captured image 400. The head part 403 may be considered a subset of data from captured image 400 that will be manipulated or analyzed to create a facial skin mask as discussed herein. Parts of the captured image 400 that are not part of the head part 403 of captured image 400, such as the body region 411, or other environmental parts of captured image 400 (e.g., chairs or windows—not shown) are removed or otherwise not considered in the analysis for obtaining the facial skin mask.

In example, the head part 403 of captured image 400 may be converted into an RGB channel. The conversion from captured YUV image to RGB image is not required, but can make the analysis easier. All steps that use an RGB image may use a YUV image. For grayscale images, like the IR image, a modification of an algorithm is used that accepts one color channel per pixel, instead of three color channels. The modified algorithm can also be tuned for IR, where, for instance, eyes are brighter.

At block 457, each pixel of the head part 403 at block 453 are analyzed to determine skin or not skin. There are input pixel values and output pixel values. An RGB (or some other color space—e.g., YUV or IR) pixel is input and its location in the head (e.g., first pixel input is R:255, G:128, B:0 and is halfway along the head bounds in X and Y), and representative pixel (or confidence/normalized pixel) is output, whose value indicative of a level of confidence of skin or not skin (e.g., if first pixel normalized value=0.05, likely not skin; if first pixel normalized value=0.95, likely desired skin). As discussed in more detail herein, an algorithm can be used to provide an output pixel value that takes into account the position of the mouth/eyelids. For example, an input pixel that is 75% down the head that has a red color is probably a mouth and in kind will get a normalized pixel value that is indicative of probably not skin for facial mask purposes, as discussed herein. Generally, the algorithm to determine that a pixel is indicative of skin (hereinafter skin pixel determination algorithm) can use more than just color or IR data. Other per-pixel information can be used, such as spatial coordinates (e.g. x/y coordinate values relative to some point in the image, or polar coordinates from a point), inferred data items such as the pixel's depth (3-D nature of the capture technology, particularly for IR). Also, if desired, neighboring pixel data can also be used to assist in output pixel value determination.

The pixels are indicative of skin based on each output pixel value being within an acceptable threshold amount. The pixel determination algorithm may be generated by using differing methods, such as machine learning, which is discussed in further detail below with regard to FIG. 6. The pixels of block 453 that are not indicative of skin are removed or otherwise not considered in the analysis for obtaining the facial skin mask.

In an example, the output value of the pixel as discussed with regard to block 457 may be normalized. "Normalize" means after getting the output from the machine learning algorithm for each individual pixel in a face ($P_i$), the mean skin for the face is calculated, where mean is equal to the following:

$$mean = \frac{\sum_{i=0}^{n-1} P_i}{n},$$

where n representing the total number of pixels in a face. Standard deviation of the face is $$std = sqrt\frac{\sum_{i=0}^{n-1} (P_i - mean)^{\wedge}2}{n}.$$

The normalized value is calculated using the following: noramlized$P_i$=($P_i$−mean)/std. Normalization is not required. The results of the per-pixel algorithm that the machine learning generates the rules for, can be used directly, or "massaged" in various ways. After the normalization, based on the assumption that a percentage (e.g., 75%) of pixels in a face are skin, a threshold is set up to interpolate (e.g., linear) the normalized pixel value to be from 0 to 1 and then scale it to be from 0 to 255. The normalized pixel value can be seen as a confidence level for the possibility that a pixel is a skin on a face. Value "0" means definitely not a skin pixel, value "255" means definitely a skin pixel. Mouth and eye lids could be some value between 0 and 122 since they are most likely not desirable for the facial skin mask, as defined herein.

Figure 7:
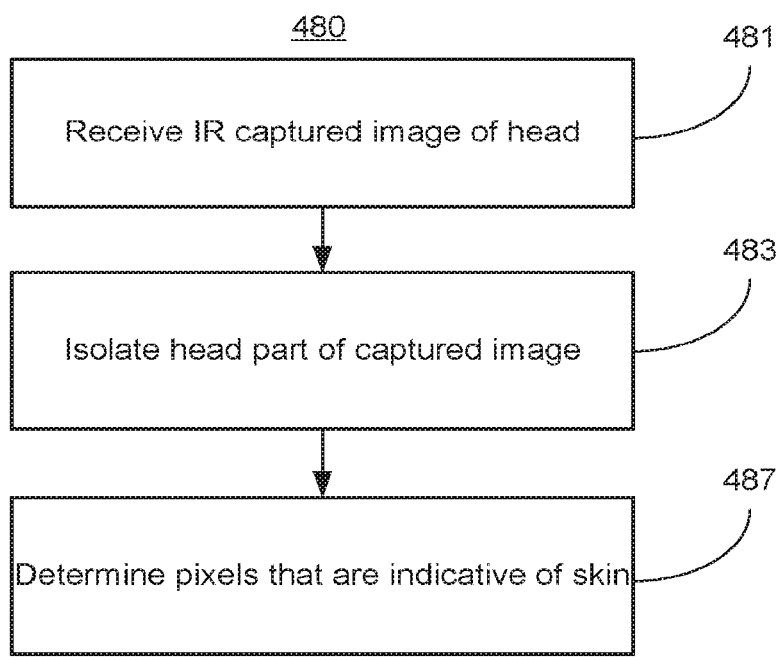
FIG. 7 illustrates an exemplary method for obtaining a facial skin mask.

At block 459, if the pixel values of block 457 are not within an acceptable threshold, a process to create a facial skin mask based on a non-visible light image (e.g., IR image) or other image source to create an acceptable facial skin mask (e.g., facial skin mask with the acceptable threshold). The determination of being within an acceptable threshold for the facial skin mask may be based on a result of a calculation of the average value of the pixels that were indicative of skin at block 457. As discussed in more detail below, FIG. 7 illustrates an exemplary method for creating a facial skin mask based on a non-visible light image, which is similar to the method herein (e.g., block 451 through block 457) as associated with creating a YUV based facial skin mask.

At block 461, the pixels used for the facial skin mask may be further to remove high velocity pixels. An optical flow technique may be used to obtain each pixel's velocity moving from frame to frame. The velocity can also be determined using other techniques. Pixels with high velocity are removed from the facial skin mask 440. The use of the optical flow techniques may result in the removal of areas that have skin. Here, the removal of a portion of the head part 403 (e.g., lips or eyelids) because of high velocity pixels may allow for more accurate output for applications that use the facial skin mask. The velocity technique can be used for any variation of skin mask generation RGB, YUV, IR, IR+depth, etc.

At block 463, the facial skin mask is created based on the resulting pixels of block 461 (or block 457 or block 459). The facial skin mask can be data that indicates the likelihood of skin or not skin from a captured image of anatomical head in a coordinate plane. The facial skin mask may be a grayscale (or color) image with approximately the same dimensions as the input head image (e.g., RGB, YUV, or IR). With regard to image of a facial skin mask, each pixel's brightness can be considered indicative of the likelihood of skin. The pixels that create the facial skin mask can be the normalized values, which can create a grayscale image. Alternatively, a facial skin mask can be a list of coordinates of pixels and corresponding output pixel values that are indicate the likelihood of skin or not skin from a captured image of anatomical head.

The facial skin mask can be generated for every frame, but does not need to be. For example, instead of generating a facial mask for each frame, if a facial skin mask is generated at time t1, several times after that (particularly associated with the same person) the generated mask at time t1 can continually be applied to subsequent frames, which may be done through interpolation or a like technique.

The created facial skin mask may be used for different applications, such as visual effects or detection of physiological changes. For example with regard to visual effects, a captured image head part 112 of the user 119 may be shown on the display 108 (FIG. 1). The captured image head part 112 may be overlaid with realistic scars and bruises on a cheek or other displayed facial skin based on the determined location of skin based on the created facial skin mask. In another example, an application may determine the heart rate of the user 119 based on examining the change of color or grayscale of the skin from frame to frame as indicated by the created facial skin mask.

Figure 6:
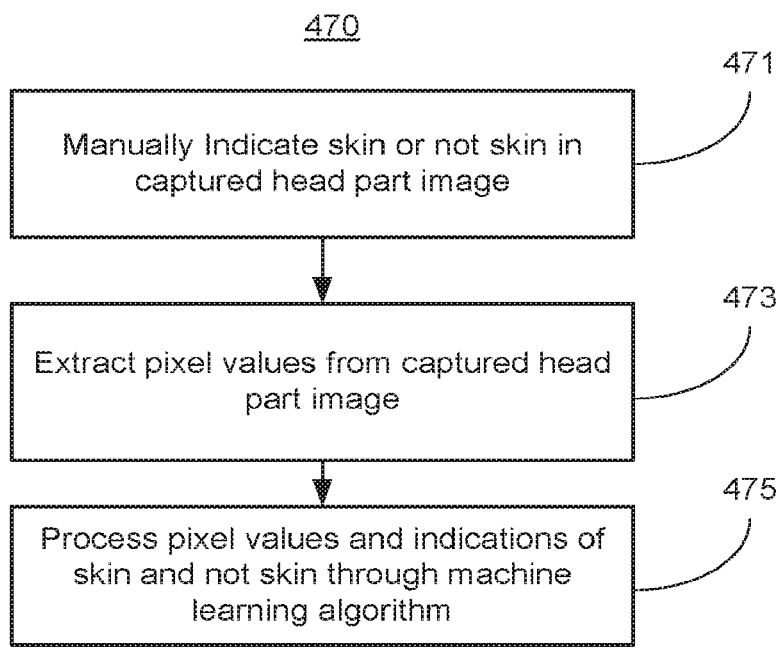
FIG. 6 illustrates an exemplary method for indicating skin.

FIG. 6 illustrates an exemplary machine learning method 470 that may be utilized to create the skin pixel determination algorithm. At block 471, skin or not skin is manually indicated for the head part 403 of captured image 400. At block 473, pixel values, such as luminance and distance from a head center may be extracted from the head part 403 of the captured image 400. At block 475, the pixel values of block 473 and the indications of skin of block 471 may be processed through a machine learning algorithm. Block 471 through block 473 may be repeated for hundreds or thousands of captured head images with differing skin tone (e.g., Fitzpatrick scale) to create the skin pixel determination algorithm, which, for this example, is machine learned. In an alternative example with regard to block 471, there may be a desire for other parts that are skin to be removed from the processing of the facial skin mask. Particular moving parts (such as blinking eyes and a chewing mouth) on the face may negatively impact the determination of a heart rate signal. To remove particular moving parts from the analysis, the mouth and eye lids, for example, may be indicated as not skin for the machine learning process (or another process) that creates the skin pixel determination algorithm. With regard to heart rate related analysis, because mouth and eye lids may be excluded using the skin pixel determination algorithm, it may be more accurately stated that the skin pixel determination algorithm outputs pixel values that indicate the likelihood of skin that is desirable for heart rate related analysis.

FIG. 7 illustrates an exemplary method 480 for creating a facial skin mask based on non-visible light captured image. At a block 481 the captured image 400 may be received. Here, it is assumed the captured image 400 is an IR based image captured by the capture device 113. At block 483, the head part 403 is isolated from the captured image 400.

At block 487, the pixels of the converted head part 403 at block 483 are analyzed to determine the likelihood of skin or not skin (similar to block 457). The pixels, which have a channel value, are indicative of skin based on the pixel value being within an acceptable threshold amount. The skin pixel determination algorithm may be generated by using differing methods, such as machine learning, which is discussed with regard to FIG. 6. The pixels of block 483 that are not indicative of skin are removed from the analysis for obtaining the facial skin mask. At block 489, the pixel value of block 487 and the pixel value of block 457 may be compared or otherwise examined together to get a further refined determination of what is likely skin or not skin for the facial skin mask. With regard to comparing images, the IR images or YUV/RGB images may be from different cameras and therefore may need to be synchronized. If captured images are from slightly different times or angles, then image registration or another technique may be used to compensate for the different times or angles in order to synchronize images. This synchronization may be needed when comparing images, as discussed herein in.

An image-based heart rate detection technique is based on the comparison of successive images of a subject from a camera. As discussed herein, facial skin can be used for heart rate detection since the change of human skin color reflects the heart rate. The face is the most common exposure skin part of the body. However, the non-skin parts (such as hair and beard) and other features (e.g., blinking eyes and chewing mouth) on a face often negatively affect the determination of a heart rate signal. Therefore, a more refined facial skin mask, as discussed herein, can be used to deliver a more accurate heart rate of a subject. A more accurate face mask can also help display better positioned visual effects on a display.

The accuracy of facial skin masks based on visible light images can be negatively affected by lighting. Discussed herein is the capturing of images using multiple sources, such as multiple visible light based image captures and non-visible light based image captures, to create a facial skin mask that more accurately identifies skin or other features of a subject for different applications, such as heart rate monitoring and displayed visual effects. In an example, multimedia console 103 or another device may detect the lighting within the physical space 116. The multimedia console may receive the detected lighting and process the captured image based on non-visible light initially before and not try to create a facial mask based on a captured image based on visible light. This may reduce the amount of processing by the multimedia console 103.

Figure 8:
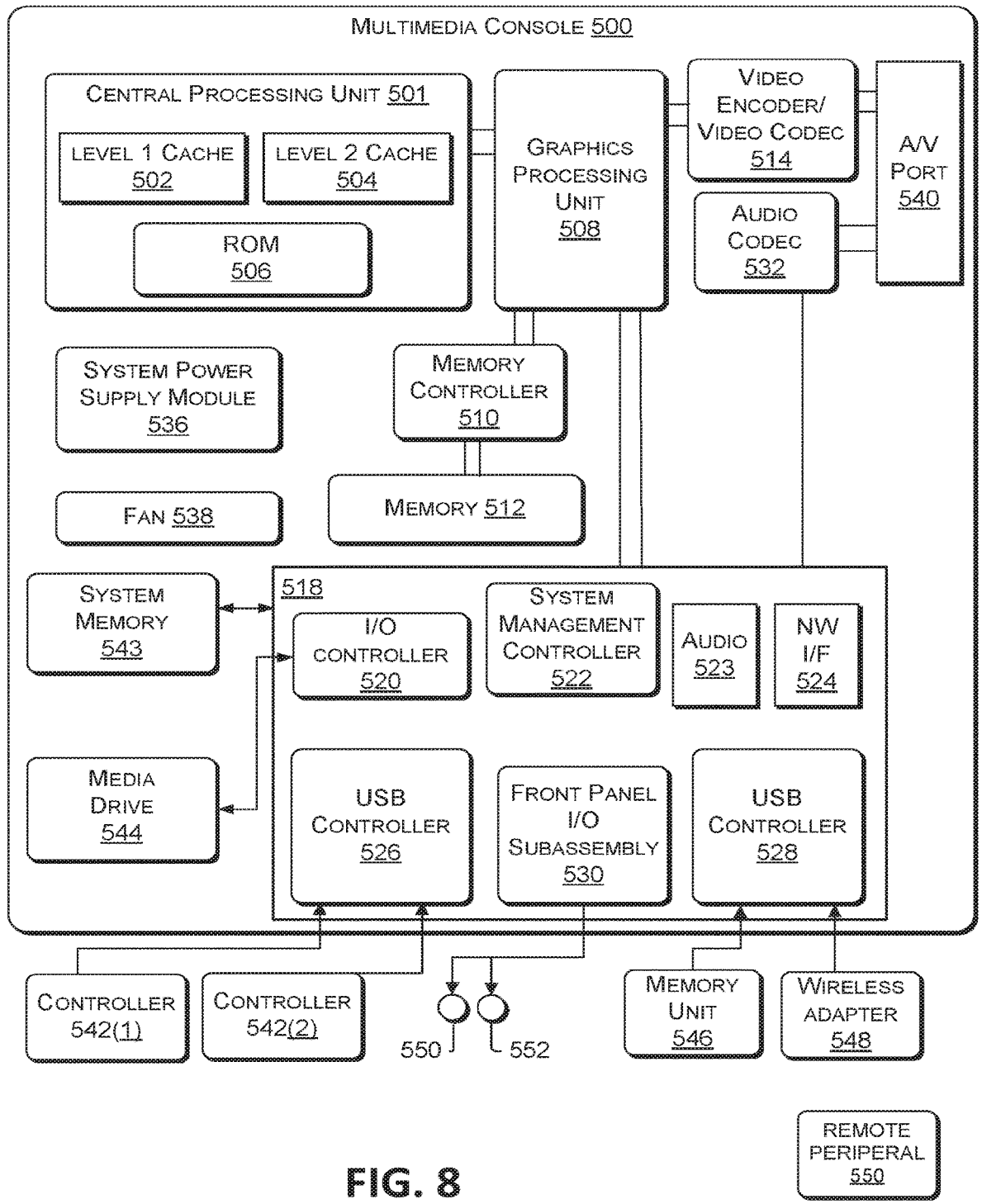
FIG. 8 shows an example block diagram of an illustrative multimedia console that may be used in part to implement the disclosed a facial skin mask.

FIG. 8 is an illustrative functional block diagram of the multimedia console 103 shown in FIG. 1. In an example, one or more method steps associated with FIG. 5-FIG. 7 are executed on the multimedia console 103, which is described in more detail in FIG. 8. In other examples, the methods associated with FIG. 5-FIG. 7 may be executed on devices such as a smart phone, a desktop computer, a netbook computer, a tablet computer, a laptop computer, or other computing devices. As shown in FIG. 8 the multimedia console 103 has a central processing unit (CPU) 501 having a level 1 cache 502, a level 2 cache 504, and a Flash ROM (Read Only Memory) 506. The level 1 cache 502 and the level 2 cache 504 temporarily store data and hence reduce the number of memory access cycles, thereby improving processing speed and throughput. The CPU 501 may be configured with more than one core, and thus, additional level 1 and level 2 caches 502 and 504. The Flash ROM 506 may store executable code that is loaded during an initial phase of a boot process when the multimedia console 103 is powered ON.

A graphics processing unit (GPU) 508 and a video encoder/video codec (coder/decoder) 514 form a video processing pipeline for high speed and high resolution graphics processing. Data is carried from the GPU 508 to the video encoder/video codec 514 via a bus. The video processing pipeline outputs data to an A/V (audio/video) port 540 for transmission to a television or other display. A memory controller 510 is connected to the GPU 508 to facilitate processor access to various types of memory 512, such as, but not limited to, a RAM.

The multimedia console 103 includes an I/O controller 520, a system management controller 522, an audio processing unit 523, a network interface controller 524, a first USB host controller 526, a second USB controller 528, and a front panel I/O subassembly 530 that are preferably implemented on a module 518. The USB controllers 526 and 528 serve as hosts for peripheral controllers 542(1)-542(2), a wireless adapter 548, and an external memory device 546 (e.g., Flash memory, external CD/DVD ROM drive, removable media, etc.). The network interface controller 524 and/or wireless adapter 548 provide access to a network (e.g., the Internet, home network, etc.) and may be any of a wide variety of various wired or wireless adapter components including an Ethernet card, a modem, a Bluetooth module, a cable modem, and the like.

System memory 543 is provided to store application data that is loaded during the boot process. A media drive 544 is provided and may comprise a DVD/CD drive, hard drive, or other removable media drive, etc. The media drive 544 may be internal or external to the multimedia console 103. Application data may be accessed via the media drive 544 for execution, playback, etc. by the multimedia console 103. The media drive 544 is connected to the I/O controller 520 via a bus, such as a Serial ATA bus or other high speed connection (e.g., IEEE 1394).

The system management controller 522 provides a variety of service functions related to assuring availability of the multimedia console 103. The audio processing unit 523 and an audio codec 532 form a corresponding audio processing pipeline with high fidelity and stereo processing. Audio data is carried between the audio processing unit 523 and the audio codec 532 via a communication link. The audio processing pipeline outputs data to the A/V port 540 for reproduction by an external audio player or device having audio capabilities.

The front panel I/O subassembly 530 supports the functionality of the power button 550 and the eject button 552, as well as any LEDs (light emitting diodes) or other indicators exposed on the outer surface of the multimedia console 103. A system power supply module 536 provides power to the components of the multimedia console 103. A fan 538 cools the circuitry within the multimedia console 103.

The CPU 501, GPU 508, memory controller 510, and various other components within the multimedia console 103 are interconnected via one or more buses, including serial and parallel buses, a memory bus, a peripheral bus, and a processor or local bus using any of a variety of bus architectures. By way of example, such architectures can include a Peripheral Component Interconnects (PCI) bus, PCI-Express bus, etc.

When the multimedia console 103 is powered ON, application data may be loaded from the system memory 543 into memory 512 and/or caches 502 and 504 and executed on the CPU 501. The application may present a graphical user interface that provides a consistent user experience when navigating to different media types available on the multimedia console 103. In operation, applications and/or other media contained within the media drive 544 may be launched or played from the media drive 544 to provide additional functionalities to the multimedia console 103.

The multimedia console 103 may be operated as a stand-alone system by simply connecting the system to a television or other display. In this standalone mode, the multimedia console 103 allows one or more users to interact with the system, watch movies, or listen to music. However, with the integration of broadband connectivity made available through the network interface controller 524 or the wireless adapter 548, the multimedia console 103 may further be operated as a participant in a larger network community.

When the multimedia console 103 is powered ON, a set amount of hardware resources are reserved for system use by the multimedia console operating system. These resources may include a reservation of memory (e.g., 16 MB), CPU and GPU cycles (e.g., 5%), networking bandwidth (e.g., 8 kbs), etc. Because these resources are reserved at system boot time, the reserved resources do not exist from the application's view.

In particular, the memory reservation preferably is large enough to contain the launch kernel, concurrent system applications, and drivers. The CPU reservation is preferably constant such that if the reserved CPU usage is not used by the system applications, an idle thread will consume any unused cycles.

With regard to the GPU reservation, lightweight messages generated by the system applications (e.g., pop-ups) are displayed by using a GPU interrupt to schedule code to render pop-ups into an overlay. The amount of memory required for an overlay depends on the overlay area size and the overlay preferably scales with screen resolution. Where a full user interface is used by the concurrent system application, it is preferable to use a resolution independent of application resolution. A scaler may be used to set this resolution such that the need to change frequency and cause a TV re-sync is eliminated.

After the multimedia console 103 boots and system resources are reserved, concurrent system applications execute to provide system functionalities. The system functionalities are encapsulated in a set of system applications that execute within the reserved system resources described above. The operating system kernel identifies threads that are system application threads versus gaming application threads. The system applications are preferably scheduled to run on the CPU 501 at predetermined times and intervals in order to provide a consistent system resource view to the application. The scheduling is to minimize cache disruption for the gaming application running on the console.

When a concurrent system application requires audio, audio processing is scheduled asynchronously to the gaming application due to time sensitivity. A multimedia console application manager (described below) controls the gaming application audio level (e.g., mute, attenuate) when system applications are active.

Input devices (e.g., controllers 542(1) and 542(2)) are shared by gaming applications and system applications. The input devices are not reserved resources, but are to be switched between system applications and the gaming application such that each will have a focus of the device. The application manager preferably controls the switching of input stream, without knowledge of the gaming application's knowledge and a driver maintains state information regarding focus switches. The capture device 113 may define additional input devices for the multimedia console 103.

Figure 9:
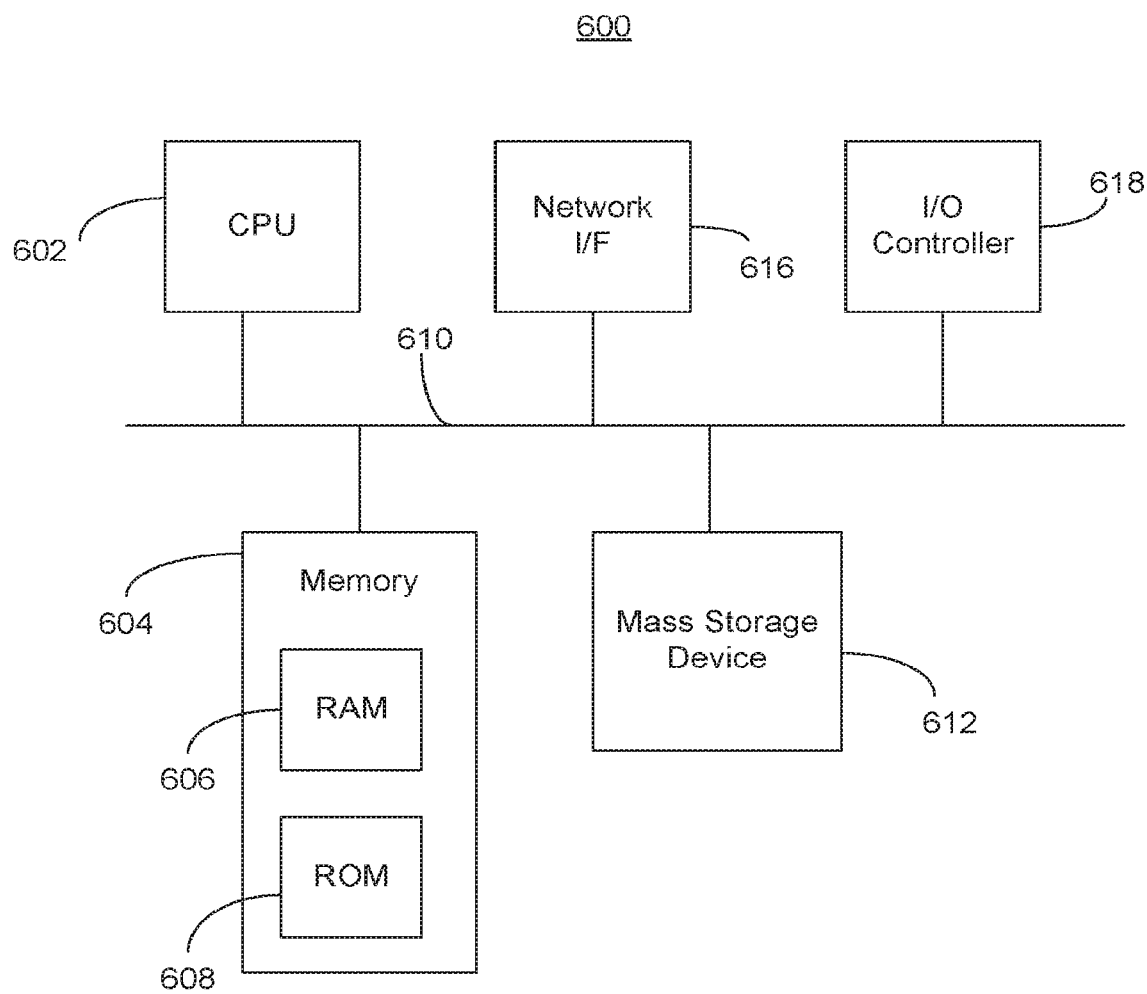
FIG. 9 shows an example block diagram of an illustrative computing platform that may be used in part to implement the disclosed a facial skin mask.

It may be desirable and/or advantageous to enable other types of computing platforms other than the illustrative multimedia console 103 to create the facial skin mask in some applications. For example, creating a facial skin mask may be readily adapted to run on fixed computing platforms and mobile computing platforms that have video capture capabilities. FIG. 9 shows one illustrative architecture 600 for a computing platform or device capable of executing the various components described herein for creating a facial skin mask and using it with other applications, such monitoring physiological changes (e.g., optical heart rate tracking) or visual effects, as discussed herein. Thus, the architecture 600 illustrated in FIG. 9 shows an architecture that may be adapted for a server computer, mobile phone, a PDA (personal digital assistant), a mobile phone, a desktop computer, a netbook computer, a tablet computer, gaming console, or a laptop computer. The architecture 600 may be utilized to execute any aspect of the components presented herein.

The architecture 600 illustrated in FIG. 9 includes a CPU 602, a system memory 604, including a RAM 606 and a ROM 608, and a system bus 610 that couples the memory 604 to the CPU 602. A basic input/output system containing the basic routines that help to transfer information between elements within the architecture 600, such as during startup, is stored in the ROM 608. The architecture 600 further includes a mass storage device 612 for storing software code or other computer-executed code that is utilized to implement applications, the optical heart rate tracking engine, facial skin mask engine, the motion tracking engine, the gesture recognition engine, the depth image processing engine, and the operating system which may be configured with functionality and operations in a similar manner to those components shown in FIG. 2 and described in the accompanying text.

The mass storage device 612 is connected to the CPU 602 through a mass storage controller (not shown) connected to the bus 610. The mass storage device 612 and its associated computer-readable storage media provide non-volatile storage for the architecture 600. Although the description of computer-readable storage media contained herein refers to a mass storage device, such as a hard disk or CD-ROM drive. It should be appreciated by those skilled in the art that computer-readable storage media can be any available computer storage media that can be accessed by the architecture 600.

Although the description of computer-readable storage media contained herein refers to a mass storage device, such as a hard disk or CD-ROM drive, it should be appreciated by those skilled in the art that computer-readable storage media can be any available storage media that can be accessed by the architecture 600.

By way of example, and not limitation, computer-readable storage media may include volatile and non-volatile, removable and non-removable storage media implemented in any method or technology for storage of information such as computer-readable instructions, data structures, program modules or other data. For example, computer-readable storage media includes, but is not limited to, RAM, ROM, EPROM (erasable programmable read only memory), EEPROM (electrically erasable programmable read only memory), Flash memory or other solid state memory technology, CD-ROM, DVDs, HD-DVD (High Definition DVD), BLU-RAY, magnetic cassettes, magnetic tape, or magnetic disk storage. Other optical storage media, magnetic storage media, or any other storage media can be used to store the desired information and which can be accessed by the architecture 600. For purposes of this specification and the claims, the phrase "computer-readable storage medium," "storage media," and variations thereof, does not include signals per se, and has a concrete, tangible, and physical structure. The memory may comprise a storage medium having a concrete, tangible, physical structure. Memory, as well as any computer-readable storage medium described herein, is not to be construed as a signal. The memory, as well as any computer-readable storage medium described herein, is to be construed as an article of manufacture.

According to various examples, the architecture 600 may operate in a networked environment using logical connections to remote computers through a network. The architecture 600 may connect to the network through a network interface unit 616 connected to the bus 610. It should be appreciated that the network interface unit 616 also may be utilized to connect to other types of networks and remote computer systems. The architecture 600 also may include an input/output controller 618 for receiving and processing input from a number of other devices, including a keyboard, mouse, or electronic stylus (not shown in FIG. 9). Similarly, the input/output controller 618 may provide output to a display screen, a printer, or other type of output device (also not shown in FIG. 9).

It should be appreciated that the software components described herein may, when loaded into the CPU 602 and executed, transform the CPU 602 and the overall architecture 600 from a general-purpose computing system into a special-purpose computing system customized to facilitate the functionality presented herein. The CPU 602 may be constructed from any number of transistors or other discrete circuit elements, which may individually or collectively assume any number of states. More specifically, the CPU 602 may operate as a finite-state machine, in response to executable instructions contained within the software modules disclosed herein. These computer-executable instructions may transform the CPU 602 by specifying how the CPU 602 transitions between states, thereby transforming the transistors or other discrete hardware elements constituting the CPU 602.

Encoding the software modules presented herein also may transform the physical structure of the computer-readable storage media presented herein. The specific transformation of physical structure may depend on various factors, in different implementations of this description. Examples of such factors may include, but are not limited to, the technology used to implement the computer-readable storage media, whether the computer-readable storage media is characterized as primary or secondary storage, and the like. For example, if the computer-readable storage media is implemented as semiconductor-based memory, the software disclosed herein may be encoded on the computer-readable storage media by transforming the physical state of the semiconductor memory. For example, the software may transform the state of transistors, capacitors, or other discrete circuit elements constituting the semiconductor memory. The software also may transform the physical state of such components in order to store data thereupon.

As another example, the computer-readable storage media disclosed herein may be implemented using magnetic or optical technology. In such implementations, the software presented herein may transform the physical state of magnetic or optical media, when the software is encoded therein. These transformations may include altering the magnetic characteristics of particular locations within given magnetic media. These transformations also may include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the architecture 600 in order to store and execute the software components presented herein. It also should be appreciated that the architecture 600 may include other types of computing devices, including hand-held computers, embedded computer systems, smartphones, PDAs, and other types of computing devices known to those skilled in the art. It is also contemplated that the architecture 600 may not include all of the components shown in FIG. 9, may include other components that are not explicitly shown in FIG. 9, or may utilize an architecture completely different from that shown in FIG. 9.

Based on the discussion herein, it should be appreciated that technologies for providing and using facial skin masks. Although the subject matter presented herein has been described in language specific to computer structural features, methodological and transformative acts, specific computing machinery, and computer-readable storage media, it is to be understood that the appended claims is not necessarily limited to the specific features, acts, or media described herein. Rather, the specific features, acts, and mediums are disclosed as example forms of implementing the claims.

Methods, systems, and apparatuses, among other things, as described herein may provide for means for determining the likelihood of skin or not skin on a face. A method, system, computer readable storage medium, or apparatus has means for receiving data of a captured image, the data of the captured image comprising a subset of data of an anatomical head, the subset of data of the anatomical head comprising a plurality of representative pixels having a respective plurality of pixel values; and means for determining whether each pixel of the plurality of representative pixels has the respective plurality of pixel values within a threshold value that is indicative of skin. The method, system, computer readable storage medium, or apparatus has means for determining whether the plurality of representative pixels average a value that is within a threshold indicative of an acceptable skin mask. The method, system, computer readable storage medium, or apparatus has means for responsive to determining that the plurality of representative pixels average a value within a threshold value indicative of skin of an acceptable skin mask, creating a facial skin mask with each pixel of the plurality of representative pixels within the threshold value that is indicative of skin. The method, system, computer readable storage medium, or apparatus has means for responsive to determining that the plurality of representative pixels average a value within a threshold value that is indicative of skin of an acceptable skin mask, determining velocity of each pixel of the plurality of representative pixels that has a plurality of respective pixel velocity values within a threshold value that is indicative of an acceptable velocity; and means for creating a facial skin mask based on each pixel of the plurality of representative pixels having: the plurality of respective pixel velocity values within the threshold value that is indicative of the acceptable velocity, and the respective plurality of pixel values within the threshold value that is indicative of skin. The plurality of respective pixel velocity values of each pixel can be based on the use of an optical flow technique. The method, system, computer readable storage medium, or apparatus has means for creating a facial skin mask with each pixel of the plurality of representative pixels that have the respective plurality of pixel values within the threshold value that is indicative of skin; and means for providing instructions to display a graphic overlay based on the facial skin mask. The graphic overlay can comprise a depiction of a scar. The method, system, computer readable storage medium, or apparatus has means for creating a facial skin mask with each pixel of the plurality of representative pixels that have the respective plurality of pixel values that is within the threshold value that is indicative of skin; and means for providing instructions to determine a heart rate based on the facial skin mask. The respective plurality of pixel values can be based on a color channel. The captured image can comprise an image based on a non-visible light.

A method, system, computer readable storage medium, or apparatus has means for receiving a first data of a first captured image, the first data of the first captured image comprising a first subset of data of an anatomical head; means for converting a first plurality of representative pixels of the first subset of data of the anatomical head to a red, green, and blue (RGB) channel, the first plurality of representative pixels having a respective first plurality of pixel values based on the RGB channel; and means for determining whether each pixel of the first plurality of representative pixels has a respective plurality of pixel values within a first threshold value that is indicative of skin. The method, system, computer readable storage medium, or apparatus has means for responsive to determining that the first plurality of representative pixels average a first value that is not within a threshold indicative of skin of an acceptable skin mask, converting a second plurality of representative pixels of a second subset of data of an anatomical head of a second captured image to a red, green, and blue (RGB) channel, each pixel of the second plurality of representative pixels having a respective second plurality of pixel values based on the RGB channel; means for comparing the first plurality of representative pixels that average the first value with the second plurality of representative pixels that average a second value; and means for creating a facial skin mask with each pixel of the second plurality of representative pixels within the threshold value that is indicative of skin based on the comparing of the first plurality of representative pixels that average the first value with the second plurality of representative pixels that average the second value. The method, system, computer readable storage medium, or apparatus has means for responsive to determining that a second plurality of representative pixels a second subset of data of an anatomical head of a second captured image average a second value within a threshold value indicative of skin of an acceptable skin mask, determining velocity of each pixel of a second plurality of representative pixels that has a plurality of respective pixel velocity values within a threshold value that is indicative of an acceptable velocity; and means for creating a facial skin mask based on each pixel of the second plurality of representative pixels having: the plurality of respective pixel velocity values within the threshold value that is indicative of the acceptable velocity, and the second respective plurality of pixel values within the threshold value that is indicative of skin. The pixel velocity value of each pixel of the second plurality of representative pixels may be based on the use of an optical flow technique.

The subject matter described herein is provided by way of illustration. Various modifications and changes may be made to the subject matter described herein without following the examples and applications illustrated and described (e.g., skipping or adding steps), and without departing from the true spirit and scope the disclosed subject matter, which is set forth in the following claims.

What is claimed:

1. A computing device, comprising:
   at least one memory and at least one processor, wherein the at least one memory and the at least one processor are respectively configured to store and execute instructions for causing the computing device to perform operations, and wherein the operations include:
   receiving data associated with multiple captured image frames, the data of each of the multiple captured image frames including a plurality of pixels;
   determining a subset of the plurality of pixels of a first frame of the multiple captured image frames, wherein the determining of the subset of the first frame is based, at least in part, on whether each particular individual pixel of the plurality of pixels of the first frame has a color value that is indicative of skin of an anatomical head;
   determining a subset of the plurality of pixels of a second frame of the multiple captured image frames, wherein the determining of the subset of the second frame is based, at least in part, on whether each particular individual pixel of the plurality of pixels of the second frame has the color value that is indicative of skin of the anatomical head;
   determining respective differences between individual color values of the individual pixels of the subset of the first frame and individual color values of the individual pixels of the subset of the second frame; and
   determining a heart rate based on the determining of the respective differences.

2. The computing device of claim 1, wherein the determining of the subset of the plurality of pixels of the first frame is also based on positions of each particular individual pixel of the plurality of pixels of the first frame.

3. The computing device of claim 1, wherein the determining of the subset of the plurality of pixels of the first frame is also based on depth of each particular individual pixel of the plurality of pixels of the first frame.

4. The computing device of claim 1, wherein the determining of the heart rate is also based on rates of change between the individual color values of the individual pixels of the subset of the first frame and the individual color values of the individual pixels of the subset of the second frame.

5. The computing device of claim 1, wherein the determining of the heart rate is also based on use of an optical flow technique.

6. The computing device of claim 1, wherein the data associated with multiple captured image frames includes information from a visible portion of a light spectrum.

7. A method, comprising:
receiving data associated with multiple captured image frames, the data of each of the multiple captured image frames including a plurality of pixels;
determining a subset of the plurality of pixels of a first frame of the multiple captured image frames, wherein the determining of the subset of the first frame is based, at least in part, on whether each particular individual pixel of the plurality of pixels of the first frame has a color value that is indicative of skin of an anatomical head;
determining a subset of the plurality of pixels of a second frame of the multiple captured image frames, wherein the determining of the subset of the second frame is based, at least in part, on whether each particular individual pixel of the plurality of pixels of the second frame has the color value that is indicative of skin of the anatomical head;
determining respective differences between individual color values of the individual pixels of the subset of the first frame and individual color values of the individual pixels of the subset of the second frame; and
determining a heart rate based on the determining of the respective differences.

8. The method of claim 7, wherein the determining of the subset of the plurality of pixels of the first frame is also based on positions of each particular individual pixel of the plurality of pixels of the first frame.

9. The method of claim 7, wherein the determining of the subset of the plurality of pixels of the first frame is also based on depth of each particular individual pixel of the plurality of pixels of the first frame.

10. The method of claim 7, wherein the determining of the heart rate is also based on rates of change between the individual color values of the individual pixels of the subset of the first frame and the individual color values of the individual pixels of the subset of the second frame relative to a threshold velocity value.

11. The method of claim 7, wherein the determining of the heart rate is also based on use of an optical flow technique.

12. The method of claim 7, wherein the data associated with multiple captured image frames includes information from a non-visible portion of a light spectrum.

13. The method of claim 7, further comprising:
creating a facial skin map from the subset of the plurality of pixels of a first frame, wherein the determining respective differences is also based on the facial skin map.

14. A computer-readable storage medium, having stored thereon processor-executable code, that, responsive to execution by at least one processor, cause a computing device to perform operations, the operations comprising:
receiving a first data associated with a first captured image including a first subset of data of an anatomical head;
converting a first plurality of representative pixels of the first subset of data of the anatomical head to a color channel, the first plurality of representative pixels having a respective first plurality of pixel values based on the color channel;
determining, for each pixel of the first plurality of representative pixels, whether the pixel has a respective plurality of pixel values within a first threshold value that is indicative of skin;
responsive to determining that the first plurality of representative pixels average a first value that is not within a first skin mask threshold, converting a second plurality of representative pixels of a second subset of data of an anatomical head associated with a second captured image to a color channel, each pixel of the second plurality of representative pixels having a respective second plurality of pixel values based on the color channel;
creating a facial skin mask with each pixel of the second plurality of representative pixels within a threshold value that is indicative of skin based on a comparison of the first plurality of representative pixels that average the first value with the second plurality of representative pixels that average a second value; and
determining a heart rate based on color of the pixels of the facial skin mask.

15. The computer-readable storage medium of claim 14, wherein the operations further comprise:
displaying a graphic overlay based on the facial skin mask.

16. The computer-readable storage medium of claim 14, wherein the creating of the facial skin mask is further based on each pixel of the second plurality of representative pixels having a plurality of respective pixel velocity values within a threshold velocity value.

17. The computer-readable storage medium of claim 16, wherein the plurality of respective pixel velocity values of each pixel of the second plurality of representative pixels is determined using an optical flow technique.

18. The computer-readable storage medium of claim 14, wherein determining the heart rate is further based on a change in the color of pixels of the facial skin mask over time.

19. The computer-readable storage medium of claim 14, wherein the respective first plurality of pixel values is based on a position of the first plurality of representative pixels on the anatomical head.

20. The computer-readable storage medium of claim 14, wherein at least one color channel is for a non-visible portion of a light spectrum.

* * * * *